United States Patent
Clark et al.

(10) Patent No.: US 8,178,078 B2
(45) Date of Patent: *May 15, 2012

(54) COMPOSITIONS CONTAINING A SOLVATED ACTIVE AGENT SUITABLE FOR DISPENSING AS A COMPRESSED GAS AEROSOL

(75) Inventors: Paul A. Clark, Racine, WI (US); Richard S. Valpey, III, Lindenhurst, IL (US); Maciej K. Tasz, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1006 days.

This patent is subject to a terminal disclaimer.

(21) Appl. No.: 12/213,066

(22) Filed: Jun. 13, 2008

(65) Prior Publication Data

US 2009/0311195 A1    Dec. 17, 2009

(51) Int. Cl.
*A01N 25/00* (2006.01)
*A01N 25/02* (2006.01)
*A01N 25/06* (2006.01)
*A01N 25/32* (2006.01)
*A61K 8/02* (2006.01)

(52) U.S. Cl. .............. 424/45; 424/401; 424/405

(58) Field of Classification Search .......... 424/45, 424/401, 405
See application file for complete search history.

(56) References Cited

U.S. PATENT DOCUMENTS

| | | | |
|---|---|---|---|
| 3,067,024 A | 12/1962 | Boies et al. | |
| 3,433,577 A | 3/1969 | Schick | |
| 3,759,594 A | 9/1973 | Cobb | |
| 3,829,578 A | 8/1974 | Fleming et al. | |
| 3,864,471 A | 2/1975 | King et al. | |
| 3,966,087 A * | 6/1976 | Curry et al. | 222/192 |
| 3,979,617 A | 9/1976 | Thom | |
| 4,060,639 A | 11/1977 | Jacobus et al. | |
| 4,083,954 A | 4/1978 | Tsuchiya et al. | |
| 4,105,581 A | 8/1978 | Sexsmith | |
| 4,184,612 A | 1/1980 | Freyre | |
| 4,263,275 A | 4/1981 | Nandagiri | |
| 4,333,516 A | 6/1982 | Krueger et al. | |
| 4,382,078 A | 5/1983 | Berkhoff et al. | |
| 4,584,021 A | 4/1986 | Bartlett | |
| 4,668,507 A | 5/1987 | Tomkins et al. | |
| 4,676,977 A | 6/1987 | Haus et al. | |
| 4,740,366 A | 4/1988 | Winston | |
| 4,882,182 A | 11/1989 | Halls et al. | |
| 4,913,893 A | 4/1990 | Varco et al. | |
| 4,915,854 A * | 4/1990 | Mao et al. | 510/296 |
| 4,965,063 A | 10/1990 | Casey et al. | |
| 5,047,234 A | 9/1991 | Dickerson et al. | |
| 5,064,635 A | 11/1991 | Casey | |
| 5,091,111 A | 2/1992 | Neumiller | |
| 5,145,604 A | 9/1992 | Neumiller | |
| 5,266,690 A | 11/1993 | McCurry, Jr. et al. | |
| 5,449,763 A | 9/1995 | Wulff et al. | |
| 5,472,686 A | 12/1995 | Tsubaki et al. | |
| 5,489,433 A | 2/1996 | Aboud | |
| 5,494,912 A | 2/1996 | Halazy et al. | |
| 5,527,803 A | 6/1996 | Halazy et al. | |
| 5,538,978 A | 7/1996 | Halazy et al. | |
| 5,567,354 A | 10/1996 | Schwendimann | |
| 5,670,475 A | 9/1997 | Trinh et al. | |
| 5,679,324 A | 10/1997 | Lisboa et al. | |
| 5,720,983 A | 2/1998 | Malone | |
| 5,734,029 A | 3/1998 | Wulff et al. | |
| 5,859,218 A | 1/1999 | Wulff et al. | |
| 5,874,067 A | 2/1999 | Lucas et al. | |
| 5,935,554 A | 8/1999 | Tomlinson | |
| 5,962,399 A | 10/1999 | Wulff et al. | |
| 6,077,318 A | 6/2000 | Trinh et al. | |
| 6,080,387 A | 6/2000 | Zhou et al. | |
| 6,146,587 A | 11/2000 | Morgan | |
| 6,149,898 A * | 11/2000 | Peffly et al. | 424/70.12 |
| 6,180,088 B1 | 1/2001 | Ohtsubo et al. | |
| 6,238,646 B1 | 5/2001 | Zembrodt | |
| 6,248,135 B1 | 6/2001 | Trinh et al. | |
| 6,284,225 B1 | 9/2001 | Bhatt et al. | |
| 6,290,945 B1 | 9/2001 | Baker et al. | |

(Continued)

FOREIGN PATENT DOCUMENTS

| | | |
|---|---|---|
| EP | 0348091 A1 | 12/1989 |
| EP | 0462605 A2 | 12/1991 |
| EP | 0462605 A3 | 3/1993 |
| EP | 0488668 B1 | 4/1997 |
| EP | 1002549 A1 | 5/2000 |
| EP | 1577361 A1 | 9/2005 |
| EP | 1792600 A1 | 6/2007 |
| EP | 1834626 A2 | 9/2007 |
| JP | 56063913 A | 5/1981 |
| JP | 58189106 A | 11/1983 |

(Continued)

OTHER PUBLICATIONS

Merriam Webster's Collegiate Dictionary, 10$^{th}$ edition, Merriam-Webster, Inc., Springfield, MA: 1996, pp. 58.*
PCT/US2009/003452 International Search Report and Written Opinion dated Jun. 1, 2010.

*Primary Examiner* — James H. Alstrum-Acevedo

(57) ABSTRACT

A composition for solvating one or more active agents in an aqueous solution which is suitable for dispensing as a compressed gas aerosol composition is disclosed. The composition includes at least one surfactant, at least one active agent (such as a fragrance or an insecticide), and a compressed gas propellant. The at least one surfactant is preferably present in an amount from about 0.1 wt. % to about 3 wt. %. The at least one active agent is preferably present in an amount from about 0.1 wt. % to about 2 wt. %. The compressed gas propellant is preferably present in an amount from about 0.1 wt. % to about 1 wt. %. The total surfactant weight to active agent weight ratio for the composition is preferably about 1:3 to 5:1. The composition uses a reduced amount of surfactant and active agent thereby allowing for a more efficient active agent loading and a reduced stickiness or tackiness on surfaces contacted during use.

13 Claims, No Drawings

U.S. PATENT DOCUMENTS

| | | |
|---|---|---|
| 6,451,065 B2 | 9/2002 | Trinh et al. |
| 6,482,392 B1 | 11/2002 | Zhou et al. |
| 6,531,144 B2 | 3/2003 | Kashima et al. |
| 6,729,559 B2 | 5/2004 | Zanma et al. |
| 6,861,396 B2 | 3/2005 | Baker et al. |
| 6,875,732 B2 | 4/2005 | Jurek et al. |
| 6,881,757 B2 | 4/2005 | Moodycliffe et al. |
| 6,913,711 B2 | 7/2005 | McKie et al. |
| 6,984,617 B2 | 1/2006 | Holland et al. |
| 7,053,124 B2 | 5/2006 | Mercurio |
| 7,147,822 B2 | 12/2006 | Parkhurst et al. |
| 2001/0009659 A1* | 7/2001 | Pratley et al. .................. 424/45 |
| 2002/0004033 A1 | 1/2002 | Sorgenfrey |
| 2003/0005522 A1 | 1/2003 | Trinh et al. |
| 2003/0035852 A1 | 2/2003 | Pullen |
| 2003/0092593 A1 | 5/2003 | Farooq et al. |
| 2004/0026462 A1 | 2/2004 | Moshontz et al. |
| 2004/0037782 A1 | 2/2004 | Hernandez et al. |
| 2004/0063600 A1 | 4/2004 | Williams et al. |
| 2004/0067322 A1 | 4/2004 | Baker et al. |
| 2004/0132831 A1 | 7/2004 | Mercurio et al. |
| 2004/0147416 A1 | 7/2004 | Woo et al. |
| 2004/0223871 A1 | 11/2004 | Woo et al. |
| 2004/0223943 A1 | 11/2004 | Woo et al. |
| 2004/0242428 A1 | 12/2004 | Pullen |
| 2005/0019309 A1 | 1/2005 | Park et al. |
| 2005/0020698 A1 | 1/2005 | Diamond et al. |
| 2005/0037945 A1 | 2/2005 | Gygax et al. |
| 2005/0089540 A1 | 4/2005 | Uchiyama et al. |
| 2005/0124512 A1 | 6/2005 | Woo et al. |
| 2005/0165042 A1 | 7/2005 | Zhang et al. |
| 2005/0192197 A1 | 9/2005 | Man et al. |
| 2006/0030511 A1 | 2/2006 | Makins Holland et al. |
| 2006/0263236 A1 | 11/2006 | Woo et al. |
| 2006/0292111 A1 | 12/2006 | Valpey, III et al. |
| 2007/0141126 A1* | 6/2007 | Hudson et al. ................. 424/443 |
| 2008/0003185 A1* | 1/2008 | Valpey et al. ................... 424/43 |
| 2008/0016637 A1* | 1/2008 | Lim .............................. 15/207.2 |
| 2009/0202446 A1* | 8/2009 | Vlad et al. ....................... 424/45 |

FOREIGN PATENT DOCUMENTS

| | | |
|---|---|---|
| JP | 06-329510 A | 11/1994 |
| WO | 9401511 A1 | 1/1994 |
| WO | WO2004093836 A2 | 11/2004 |
| WO | WO2004093836 A3 | 11/2004 |
| WO | WO205005264 A3 | 1/2005 |
| WO | WO2005005264 A2 | 1/2005 |
| WO | 2006099687 A1 | 9/2006 |
| WO | WO 2007/125460 * | 11/2007 |

* cited by examiner

COMPOSITIONS CONTAINING A SOLVATED ACTIVE AGENT SUITABLE FOR DISPENSING AS A COMPRESSED GAS AEROSOL

FIELD OF INVENTION

The present invention relates to a composition that solvates one or more active agents into an aqueous solution, providing the active agent(s) in a clear stable microemulsion. More particularly, the invention relates to a composition for solvating an active agent in water which is suitable for dispensing as a compressed gas aerosol composition including at least one surfactant, at least one active agent, and a compressed gas propellant, wherein the composition includes low amounts of the at least one surfactant and the at least one active agent. The total surfactant to active agent ratio is reduced to allow for more efficient loading of the active agent, and thus reduced stickiness. Preferred active agents are fragrances and insecticides.

BACKGROUND OF INVENTION

Active components or compositions, such as fragrance oils, insecticides, medicines, cleaners, polishes, hair sprays, cosmetics, paints, and the like are often composed of materials that are insoluble in water. These active components and compositions are used in the manufacture of aerosol compositions. Such active components and compositions usually require the inclusion of solvents to produce a homogeneous blend in water.

Further, aerosol compositions are generally pressurized with hydrocarbon propellants. For many reasons, including environmental concerns, industries are replacing hydrocarbons in aerosol compositions with compressed gas. However, compressed gas aerosol compositions have typically had several problems, including, but not limited to, not being able to produce stable aqueous mixtures of fragrance oils, insecticides, medicines, cleaners, polishes, hair sprays, cosmetics and paints. Due to this problem, most compressed gas aerosol compositions produced today contain materials to help dissolve or disperse these "active" ingredients. Typically, these materials are mixtures of surfactant(s) and solvent(s). The solvent(s) are often volatile organic compound(s) (VOC(s)). Alcohols, such as ethanol and isopropyl alcohol are common solvents used in these compositions. Glycols and their derivatives are also used as solvents in these compositions.

Since fragrance oils, insecticides, cleaners, polishes, hair sprays, cosmetics, and the like are composed of materials that are insoluble in water, solvents have previously been added to such compositions to increase the overall solubility of these materials.

These compositions may be dispensed by various mechanisms including aerosol dispensers or pump propelled dispensers. The compositions may contain propellants such as hydrocarbon propellants which are considered to be VOCs. The content of VOCs in aerosol compositions is regulated by Federal and/or State regulatory agencies, such as the Environmental Protection Agency (EPA) and the California Air Resources Board (CARB). One way to reduce the VOC content in such aerosol compositions is to reduce the content of the hydrocarbon propellant used to dispense the liquid product. Additionally, the desirability of VOC-free aerosol systems has created a need for stable emulsions not containing solvents.

Currently, known aerosol compositions such as air sanitizers contain hydrocarbon propellants in the amount of approximately 29.5% by weight of the contents along with 6% to 8.8% glycol levels and pure alcohol solvent. However, a reduction in the hydrocarbon propellant content can adversely affect the product performance. Specifically, reducing the propellant content in the aerosol air sanitizer may result in excessive product remaining in the container at the end of the life of the dispenser assembly (product retention) and an increase in the size of particles of the dispensed product (increased particle size). Therefore, it is desirable to use a lower amount of propellant in a composition and also ultimately to use as a result, lower amounts of surfactant and active agent, such as a fragrance or insecticide, in the composition. It is desirable to use lower amounts of these components in order to reduce the amount of expensive chemical components which reduces manufacturing costs of the product and also reduces the amount of chemicals released into the atmosphere.

One known non-aerosol air freshener composition, manufactured by S.C. Johnson & Son, Inc., includes water, a fragrance, an ethoxylated alcohol, a polyethoxylated hydrogenated castor oil, a bactericide, and an anti-foaming agent. The surfactants are present in an amount in relation to the fragrance in a ratio of 1.75:1.

U.S. Patent Application Publication No. 2002/0004033 Al describes an emulsion-type composition which provides sustained release of vapors of an active material, such as an air freshener, medicaments, repellants, etc. The compositions include water, an active air treatment ingredient to be vaporized, and an emulsifying agent in an amount to keep the active ingredient emulsified in the water in a form having an emulsion consistency without formation of a solid. The emulsifying agents (surfactants, viscofiers, thickening agents, emulsifiers) can be a single agent or a mixture of agents which result in an oil-in-water emulsion. The emulsifying agents stabilize the oil droplets of the oil phase in the water phase and the emulsifying agents do not dissolve the oil in the water to form a solution. Fragrance chemicals may be mixed with various solvents, diluents, oils, waxes, surfactants or other substances which act to dissolve the fragrance chemicals or alter their intensity, stability, viscosity, rate of release or other physical or chemical characteristics.

U.S. Patent Application Publication No. 2004/0132831 A1 and U.S. Pat. No. 7,053,124 B2 describes an aerosol delivery system stated to reduce the amount of surfactant included therein. The composition includes from 0.1-10 wt. % of a biliquid foam, 20-95 wt. % of an aqueous phase, 5-40 wt. % of a propellant and at least one oil-soluble functional material, e.g. a fragrance. The biliquid foam includes 70-95 wt. % of oil-soluble functional material and 5-30 wt. % of a continuous phase, which is preferably an aqueous phase. A surfactant may be included to stabilize the biliquid foam in an amount of 0.1-3 wt. %. Suitable surfactants disclosed are polyethoxylated hydrogenated castor oils. Surfactants may be chosen to create an affinity with the propellant. The aerosol composition is stated to eliminate the need for the use of large amounts of solvents or surfactants and volatile organic compounds. The compositions can be used, among other things, as air fresheners. The air fresheners may contain additional conventional components.

U.S. Pat. No. 6,984,617 B2 describes a composition including a fragrance-releasing complex of an entrapment material and a fragrance, and an encapsulation material, which provides improved fragrance capture and retention. The encapsulation material coats the fragrance-releasing complex to retain the fragrance in the complex state. The encapsulation material may be a nonionic surfactant such as partially or fully hydrogenated polyoxyethylene castor oil ethers. The encapsulation material may serve to prevent other materials from displacing the fragrance by solubilizing those materials. The entrapment material is used to control the release of the fragrance oils by physically surrounding and entrapping small fragrance droplets within a resistant wall. The composition is described for use in personal care products for delivery of the fragrance to hair and/or skin. The weight ratio of the fragrance-releasing complex to the encapsulation material is 1:0.1 to 1:0.9. The composition may also contain water, in which case a volatile nonaqueous solvent will also be present.

U.S. Pat. No. 4,083,954 describes an aerosol composition with a water-alcohol base to give emulsion stability to a propellant. The composition includes (A) 15-80 wt. % of a liquid propellant and (B) 85-20 wt. % of a liquid composition containing (i) 30-80 wt. % based on the weight of (B) of an alkanol with 1-3 carbon atoms, (ii) 0.05-1.0 wt. % based on the weight of B of an emulsifier consisting of an adduct of 1-300 moles of ethylene oxide to a substance selected from a group including hydrogenated castor oil, (iii) 0.01-20 wt. % based on the weight of B of an active component, and (iv) a balance of water. The alkanol is stated to dissolve a water-insoluble active component in the composition. The composition can be used as an air freshener.

U.S. Pat. No. 5,047,234 describes an aqueous air freshener composition including an inorganic salt to produce a more uniform evaporation rate of a perfume also present in the composition. The composition can contain 0.01-0.5 wt. % of the salt, 3-15 wt. % of a volatile solvent, 2-15 wt. % of an emulsifier, 1-20 wt. % of a fragrance, a balance of water and, optionally, 0-15 wt. % of a co-solvent. The salt can be an alkali metal, such as potassium, and an anionic portion, such as phosphate. The salt is stated to provide stabilizing effects, i.e., inhibition of phase separation and/or extension of the use life of the air freshener via a decrease in the rate of evaporation. Lowest ratio of surfactant to solvent disclosed therefore is 6:1.

U.S. Pat. No. 5,935,554 describes an aerosol space spray which is not an emulsion containing an active ingredient (e.g. perfume) and a propellant. The active ingredient solvates the propellant. A solvent may or may not be present.

U.S. Pat. Nos. 4,965,063 and 5,064,635 describe a cleaning composition for surfaces which contains a disappearing dye which can include a germicide. The dye is pH sensitive so that upon exposure to air the dye disappears. The composition includes about 0.1%-20.0% surfactant or mixture of surfactants and 0.05%-0.07% of a dye. The balance of the composition can be made up with water. The composition can be foamed if packaged in the appropriate delivery system. Propellant is added to the system. A propellant system in the amount of about 5%-7% will convert the liquid surfactant to a foam.

U.S. Pat. Nos. 5,091,111 and 5,145,604 describe an emulsion system which contains vesicle structures that can be used to provide reservoiring effects for the propellant component of an aerosol delivery system. The aqueous emulsion preparation can be used for delivering an aerosol composition from a pressurized container. The aqueous aerosol delivery system includes the aqueous emulsion stage component, which is present in between 75%-98% by weight of a system, and a propellant component, which is in between 2%-25% by weight of the system.

U.S. Pat. No. 5,679,324 describes a low stinging and low burning aerosol foamable fragrance composition, translucent in its pre-dispensed state, which upon discharging from an aerosol container, forms a fast-breaking foam. The composition contains a surfactant, a propellant, a fragrance, a thickener, and a cosmetic vehicle wherein the ratio of the surfactant to propellant is from about 1:1 to about 1:10.

U.S. Pat. No. 6,875,732 B2 describes a micro-emulsified fragrance composition which provides an effective fragrance delivery system when present in a laundry composition or when delivered from a substrate. The fragrance delivery system includes, by weight, (a) 2-50% of an active fragrance, (b) 50-98% of a microemulsion concentrate including (i) 0.03-80% of a nonionic surfactant, (ii) 0.002 40% of a N—$C_8$—$C_{18}$ alkyl pyrrolidone, (iii) 0-60% of a N—$C_1$—$C_4$ alkyl pyrrolidone, (iv) 0-30% of an ethylene oxide/propylene oxide block copolymer and (v) 0-10% of an ethoxylated phosphoric acid ester.

U.S. Patent Application Publication No. 2004/0147416 A1 describes a method of removing malodor from fabrics, stable aqueous odor counteractant composition and articles comprising the composition and instructions for the method and/or benefits to be derived. The composition includes malodor counteractants such as cyclodextrin, wherein the cyclodextrin being protected from interaction with any other materials that might be present in the composition so as to maintain the cyclodextrin in uncomplexed form and/or, optionally, zeolites, clay, odor blockers, odor reactants such as Class I and/or Class II aldehydes, essential oil including flavinoid, metallic salt, water soluble anionic polymer, etc. to control odor. Optionally, the composition can also contain low molecular weight polyols, chelating agents, etc. The composition is said to be preferably essentially free of any material that would soil or stain fabric.

U.S. Patent Application Publication No. 2005/0037945 A1 describes fragrance compositions to be distributed by an aerosol generator. The fragrance composition includes 30% by weight or more of a component of the odor class A, wherein the components are characterized by a sensory threshold concentration that is 1 ng/l or higher and a vapor pressure that is 10 μg/l or higher.

U.S. Patent Application Publication No. 2006/0292111 A1 describes an air treating composition for eliminating odors from air in combination with specific spray valve and actuator requirements and spray performance parameters providing maximum dispersion of the active component in the composition into the air. The particles of the composition are small so that the active component is dispersed into the air as a fine dispersion to provide more contact with odors and to provide quick absorption of odors. Particle size of the composition is controlled through the selection of valve and actuator dimensions. The air treating and odor eliminating composition includes water, a low molecular weight polyol, an emulsifier, and a propellant. The composition may also include additional adjuvants such as solvents, fragrances, corrosion inhibitor, pH adjuster and the like.

U.S. Pat. No. 4,382,078 describes a two-phase water-based aerosol composition including an active ingredient, a surfactant, a stabilizer and dimethylether (DME) propellant. The surfactant is a block copolymer of ethylene oxide and propylene oxide of a specified formula. Perfumes, insecticides, bactericides, fungicides, herbicides or deodorizing agents may be included in the composition.

U.S. Pat. No. 6,238,646 B1 describes aqueous aerosol compositions for the delivery of atomized oil, such as a fragrance oil, insecticide oil and medicinal oil. The composition includes water, a water-soluble propellant such as dimethylether, dispersed oil phase in water, nonionic surfactant and a polymeric emulsifier. The nonionic surfactant is stated to help suspend the oil particles by decreasing the droplet size of the dispersed phase in the water.

U.S. Patent Application Publication No. 2004/0209795 A1 (which corresponds to WO 2005/093836 A2) describes a perfume composition in the form of a highly transparent VOC-free microemulsion. The microemulsion includes an oil (such as a perfume oil); a surfactant system including one or more ionic surfactants and one or more nonionic surfactants; a solubilizing aid and water. The oil may contain a solvent. The ionic surfactants can be anionic, cationic or amphoteric. The amount of surfactant system present is stated to be dependent on essentially the amount of oil and solubilizing aid present and the amount necessary to provide a microemulsion. The solubilizing aid can be an organic or inorganic salt, such as selected from the group consisting of ammonium, alkaline and alkaline earth salts of $C_1$ to $C_{15}$ mono- and dicarboxylic acid derivatives, bicarbonates, halogenates, thiocyanates, and mixtures of the salts.

U.S. Patent Application Publication No. 2005/0020698 A1 (which corresponds to WO 2005/005264 A2) describes an aerosol product without a vapor tap and having a more stable emulsion using a significantly lower ratio of propellant to product. The more stable emulsion is provided by tailoring a surfactant system to other ingredients of the formulation while using decreasing percentages by weight of the propellant and eliminating the vapor tap from the valve. The aerosol products can be flying insects insecticides, room fogger insecticides and air sanitizers. The functional ingredient provides a scent, or insecticidal, germicidal or other function. Examples disclosed include water, a corrosion inhibitor, perfume oil, surfactant(s) and a hydrocarbon propellant.

U.S. Patent Application Publication No. 2003/0005522 A1; and U.S. Pat. Nos. 6,451,065; 6,248,135; 6,077,318, and 5,670,475 describe an aqueous composition for reducing malodor impression including perfume and an aqueous carrier and optionally a solubilizing aid, cyclodextrin and a metallic salt. The solubilizing aid is to solubilize any excess organic materials, in particular the perfume and other optional ingredients added, such as an insect repelling agent. A suitable solubilizing aid is a surfactant, which can be nonionic, cationic, amphoteric, zwitterionic or mixtures thereof. Anionic surfactants are stated to not be preferred because they form water-insoluble salts with metal ions of metallic salts. The composition can be dispensed from a spray dispenser which may be an aerosol using a propellant such as compressed air.

U.S. Pat. Nos. 5,734,029; 5,266,690; 5,449,763; 5,859,218, and 5,962,399 describe alkylpolyglycoside compositions having enhanced surfactant properties and containing mixtures of alkylpolyglycosides of differing alkyl chain lengths, varying degrees of polymerization and surfactant properties. The surfactant alkylpolyglycosides are stated to be useful in personal care, cosmetic, detergent, household and industrial uses. The alkylpolyglycoside mixture is stated to have improved critical micelle concentration (CMC) and interfacial tension (IFT) properties which are useful in emulsification and solubilization.

U.S. Pat. No. 6,729,559 B2 describes an aerosol product including a container holding an aerosol composition. The aerosol composition is a concentrate (a liquid containing an effective ingredient) and a propellant. The effective ingredient can be an insecticide or fragrance. The propellant can be a compressed gas such as carbon dioxide, nitrogen, nitrogen suboxide or air. The concentrate may be a spray foam containing a foaming agent such as a surfactant.

U.S. Patent Application Publication No. 2005/0124512 A1 describes an air and fabric freshener that may contain a perfume and a compressed gas, such as air. The perfume ingredients and any malodor counteractant ingredients can include any suitable percentage and the balance can be a carrier and any optional ingredient such as surfactants.

U.S. Pat. Nos. 5,538,978; 5,494,912, and 5,527,803 describe purine nucleoside phosphorylase inhibitors. These compounds can be administered as injectable dosages of the compound in a physiologically acceptable diluent. The diluent may be a surfactant, which can be a single component or a mixture, such as high molecular weight adducts of ethylene oxide with a hydrophobic base. The compound can also be administered as an aerosol or spray composition. The spray composition can also contain a surfactant and be applied by means of a propellant under pressure or by means of a compressible plastic spray bottle, nebulizer or atomizer without the use of a gaseous propellant.

European Patent Application No. 0 488 668 A1 describes a herbicide-containing liquid including a surfactant. The surfactant is to provide foaming and can be cationic, anionic, nonionic, or amphoteric. Diluents to dissolve or suspend the herbicide and surfactant can also be used, such as water, alcohol, ethylene glycol and glycol ethers. The liquid can be applied as an aerosol. The herbicide, surfactant and diluent will be enclosed in an aerosol container together with a propellant, such as a compressed gas (e.g., carbon dioxide, nitrogen gas, nitrous oxide and air).

U.S. Pat. No. 5,489,433 describes an insecticide composition including hydroxyl acyclic acid (as the active) and any ionic or nonionic surfactant. The composition can be delivered in aerosol form. The purpose of the surfactant is stated to be to reduce the surface tension of the insecticidal composition so that when the composition is applied to the body of an insect, the penetration of the hydroxyl acyclic acid into the insect's nervous system is facilitated so as to disrupt normal respiratory function of the insect and thereby suffocate the insect.

U.S. Pat. No. 3,829,578 describes an active antiviral compound which is useful with conventional pharmaceutical carriers, e.g., water, with or without the addition of a surfactant. The active compound can be packaged as an aerosol with a gaseous or liquefied propellant, e.g., carbon dioxide, with the usual adjuvants such as solvents or wetting agents. Typical surface active ingredients which can be used include high molecular weight alkyl polyglycol ethers.

U.S. Patent Application Publication No. 2005/0192197 A1 describes a peroxycarboxylic acid for reducing a population of microorganisms. Various solubilizers can be used with the acid, including various surfactants. A foaming composition is described which includes the acid compound and foaming surfactants, such as alcohol ethoxylates and alkyl ether sulfates. At the time of use, compressed air can be injected into the mixture.

U.S. Patent Application Publication No. 2005/0165042 A1 describes an active heterocyclic compound which may be administered by injection. The composition to be injected can contain a nonionic surfactant in conjunction with the heterocyclic compound. The surfactant can be a single component.

U.S. Patent Application Publication No. 2005/0089540 A1 describes a composition for application to surfaces for providing controlled release of a microencapsulated active ingredient, such as a perfume. The composition can include an aerosol propellant, such as compressed air. In addition to the perfume and propellant, the composition can include a stabilizer, such as isopropyl myristate, a dispersant and an aqueous carrier. The dispersant serves to suspend the microencapsules in the composition. The composition can optionally include a surfactant or a mixture of surfactants.

The above-described compositions have various shortcomings. These and other shortcomings of the compositions are addressed by the present invention.

SUMMARY OF THE INVENTION

The invention relates to a composition that solvates one or more active agents into an aqueous solution, providing the active agent(s) in a clear stable microemulsion. The composition is particularly suitable for dispensing as a compressed gas aerosol composition. The composition utilizes reduced amounts of surfactant and active agent with respect to the ratio of total surfactant to active agent present in the composition. The total surfactant to active agent ratio, based on weight, is preferably about 1:3 to about 5:1, more preferably about 1.2:1 to about 3:2. Such reduction provides for a more efficient active agent loading. Further, due to the reduction in component amounts, the compositions of the invention have reduced stickiness upon dispensing by compressed gas. Compressed gas dispensed compositions, dispensed by conventionally known compressed gas dispensing devices, generally have greater particle sizes as compared to standard aerosols resulting in the dispensed spray composition providing a stickiness or tackiness on surfaces upon which the particles contact following application over prolonged use. This affect is decreased with the compositions of the invention.

The composition preferably includes from about 0.1 wt. % to about 3 wt. % of at least one surfactant, from about 0.1 wt. % to about 2 wt. % of at least one active agent, and about 0.1 wt. % to about 1 wt. % of a compressed gas propellant. The active agent is preferably a fragrance, insecticide, medicament, germicide, repellant, odor eliminator, and/or the like. These active agents are water-insoluble or water-immiscible generally and, thus, the need for solvating the active agent. If not solvated, the active agent provides an undesired yielding of free oils or cloudy emulsions. Preferred embodiments are when the active agent is a fragrance or an insecticide. When the active agent is one or more fragrances and/or insecticides, the active agent is present in an amount of about 0.2 to about 2 wt. % of the total composition. The composition may also comprise other adjuvants, such as one or more of corrosion inhibitor(s), pH controller(s), solvent(s), antimicrobial(s), carrier solvent(s), processing aid(s), thickener(s), thixotrope(s), dye(s), and/or the like. The composition may be dispensed using a conventionally known compressed gas aerosol device.

A better understanding of these and other aspects, features and advantages of the invention may be had by reference to the accompanying detailed description, in which preferred embodiments of the invention are illustrated and described.

DETAILED DESCRIPTION OF THE INVENTION

The invention relates to a composition that solvates, i.e., dissolves or disperses, one or more active agents, e.g., water insoluble or water-immiscible component(s), of the composition into an aqueous solution, providing a clear or substantially clear stable microemulsion of the active agent(s). The composition is preferably a low (4% or less) volatile organic compound (VOC) or VOC-free compressed gas aerosol composition. The composition comprises at least one surfactant, at least one active agent and at least one compressed gas propellant. The composition utilizes reduced amounts of surfactant and active agent. The surfactant and active agent are present with respect to each other in a ratio of total surfactant weight % to active agent weight % of about 1:3 to about 5:1, preferably about 1:1 to about 3:2. The active agent is preferably a fragrance, insecticide, medicament, germicide, repellant, sanitizer, odor eliminator, and/or the like. The composition has significantly reduced stickiness or tackiness as to surfaces which it contacts following spray application over prolonged use due to the reduced amounts of surfactant in the composition.

The composition is in particularly suitable for dispensing as a compressed gas aerosol composition, such as an air freshener, insecticide, insect repellant and/or the like. The composition may be dispensed using a conventionally known compressed gas aerosol device. Since compressed gas aerosols devices generally provide a spray having a particle size greater than standard aerosol packages, the reduction in stickiness or tackiness of the composition as described above provides significant improvement and advantage over previously known compressed gas aerosol compositions.

The composition preferably includes from about 0.1 wt. % to about 3 wt. % of at least one surfactant, from about 0.1% to about 2% of at least one active agent, and about 0.1 wt. % to about 1 wt. % of at least one compressed gas propellant.

The composition is especially suitable for dispensing fragrances into the surrounding atmosphere. When the active agent is one or more fragrances and/or one or more insecticides, the fragrance(s) or insecticide(s) is(are) preferably present in a range of about 0.1 to about 2 wt. % of the total composition, more preferably from about 0.3 to about 0.6 wt. %, and most preferably about 0.5 wt. %

The surfactant is present in relation to the active agent, based on weight %, in a ratio of from about 1:3 to about 5:1, more preferably from about 1:1 to about 3:2. This ratio range provides for a reduction in the amount of total surfactant to active agent, e.g. fragrance, which thereby provides for a more efficient loading of the active agent. The composition may also include other adjuvants, such as one or more corrosion inhibitor(s), pH controller(s), solvent(s), antimicrobial(s), processing aid(s), thickener(s), thixotrope(s), and/or the like.

In the composition of the invention, the at least one surfactant may be a single surfactant or a blend of surfactants. The at least one surfactant is present in an amount from about 0.1 wt. % to about 3 wt. %, preferably from about 0.3 wt. % to about 2 wt. % and more preferably from about 0.5 wt. % to about 1 wt. %. The active agent is present in an amount from about 0.1 wt. % to about 2 wt. %, preferably from about 0.1 wt. % to about 1 wt. % and more preferably from about 0.3 wt. % to about 0.6 wt. %. The compressed gas propellant is present in an amount from about 0.1 wt. % to about 1 wt. %, preferably from about 0.5 wt. % to about 1 wt. % and more preferably from about 0.6 wt. % to about 0.8 wt. %.

Additionally, as to adjuvants which are optionally present, such are generally present as follows: corrosion inhibitor(s) in an amount from about 0.05 wt. % to about 1 wt. %; solvent(s) in an amount from about 0.1 wt. % to about 10 wt. %; antimicrobial(s) in an amount from about 0.05 wt. % to about 0.2 wt. %; and pH controller(s) in an amount suitable to achieve the desired pH. If other adjuvants are present, such are each generally present in an amount of about 0.0001 wt. % to about 4 wt. %.

The at least one surfactant may be any suitable surfactant or blend of surfactants based on compatibility with the active ingredient and include nonionic, cationic, anionic and/or amphoteric. Specific surfactants suitable for use alone or in a blend include, but are not limited to, polyethoxylated hydrogenated castor oil, (e.g., TAGAT-CH60 (60 ethylene oxide (EO) groups); TAGAT-CH40 (40 EO)); hydrogenated and ethoxylated castor oil blend (e.g., EUMULGIN HPS (40 EO)); secondary alcohol ethoxylate (e.g., TERGITOL 15-S-12 and TERGITOL 15-S-7); polyglyceryl-10 laurate (e.g., DERMOFEEL G10L); polyglyceryl-6 caprylate (e.g., DERMOFEEL G6CY); ethoxylated linear alcohol (e.g., LUTENSOL A08 (8 EO)); sorbitan monooleate (e.g., SPAN 80); polyoxyethylene (20) sorbitan monooleate (e.g., TWEEN 80); polyoxyethylene (20) sorbitan monolaurate (e.g., TWEEN 20); alkyl $C_9$-$C_{11}$ polyglycoside (e.g., APG 325 NK); didecyldimethylammonium chloride (e.g., BTC 1010); didecyldimethylammonium carbonate (e.g., UNIQUAT 22C50); polyethyleneoxide/polypropyleneoxide (e.g., PLURONIC F68, PLURONIC F108); and mixtures thereof.

The active agent may be any suitable fragrance, insecticide, germicide, medicament, sanitizer, odor eliminator and/or the like. An "active" agent is understood to be a chemical agent capable of activity in that it exerts some force or effect. Further, the active agent is understood to be water insoluble or water immiscible.

A fragrance suitable for use as an active agent may be any suitable natural or synthetic fragrance, based on a single component or blend of components. Fragrances are available commercially from fragrance manufacturers such as Takasago, International Flavors & Fragrances Inc., Quest, Firmenich, Givaudan, Symrise and the like.

The insecticide may be natural pyrethrins and pyrethrum extract, and synthetic pyrethroids. Insecticides suitable for use include, but are not limited to, propoxur; MGK 264; imiprothrin; sumithrin; Pynamin Forte®; neo-pynamin Forte®; cypermethrin; permethrin; cyfluthrin; acrinathrin; allethrin, such as D-allethrin; Pynamin®; benfluthrin; bifenthrin; bioallethrin such as S-bioallethrin; esbiothrin; esbiol; bioresmethrin; cycloprothrin; beta-cyfluthrin; cyhalothrin; lamda-cyhalothrin; cypermethrin; alpha-cypermethrin; beta-cypermethrin; cyphenothrin; deltamethrin; empenthrin; esfenvalerate; fenpropathrin; fenvalerate; flucythrinate; tau-fluvalinate; kadethrin; phenothrin; prallethrin, such as Etoc®; resmethrin; tefluthrin; tetramethrin or tralomethrin; other volatile insecticides as described in U.S. Pat. No. 4,439,415 can also be employed.

Table 1 sets forth various insecticide additives and the physical state thereof.

TABLE 1

Insect additives and physical state

| Chemical Name | Physical State |
|---|---|
| Sample 1 - Cyfluthrin | Solid |
| Sample 2 - Propoxur | Powder |
| Sample 3 - MGK 264 | Liquid |
| Sample 4 - Pyrethrum Extract | Liquid |
| Sample 5 - Permethrin | Crystalline |
| Sample 6 - Cypermethrin | Resin |
| Sample 7 - Imiprothrin | Liquid |
| Sample 8 - Quest Q-9633 | Liquid |
| Sample 9 - Neo-Pynamin | Powder |
| Sample 10 - Sumithrin | Liquid |
| Sample 11 - Pynamin Forte | Liquid |

Cyfluthrin is α-cyano-3-phenoxy-4-fluorobenzyl-2,2-dimethyl-3(2,2-dichlorovinyl) cyclopropanecarboxylate, from Nanjing Agrovance Chemical Industry Ltd.
Propoxur is 2-(1-methylethoxy)phenol methyl carbamate, from the Agricultural Chemicals Division of Mobay Chemical Corporation, under the trademark BAYGON TECHNICAL.
MGK 264 is N-octyl bicycloheptane dicarboximde from McLaughlin Gormley King Company.
Pyrethrum Extract is a natural extract from chrysanthemum cinerariifolium flower heads, from AJE GmbH.
Permethrin is a 3-(2,2-Dichloroethenyl)-2,2-dimethylcyclopropanecarboxylic acid (3-phenoxyphenyl)methyl ester; i.e., a 3-phenoxybenzyl (1RS)-cis,trans-3-(2,2 dichlorovinyl)-2,2 dimethyl-cyclopropane carboxylate, from Sumitomo.
Cypermethrin is a cyano(3-phenoxyphenyl)methyl 3-(2,2-dichloroethenyl)-2,2-dimethyl-cyclopropane-carboxylate, from Nanjing Agrovance Chemical Industry Ltd.
Imiprothrin is a [2,5-dioxo-3-(2-propynyl)-1-imidazolidinyl]methyl (1R)-2,2-dimethyl-3-(2-methyl-1-propenyl)cyclopropanecarboxylate, from Sumitomo.
Quest Q-9633 is a formulated mixture of a water conditioning agent and activator designed to enhance pesticide performance by modifying factors such as pH and hard water, from Helena Chemical Co.
Neopynamin Forte ® is 1,3,4,5,6,7-hexahydro-(1,3-dioxo-2H-isoindol-2-yl)methyl 2,2-dimethyl-3-(2-methyl-1-propenyl)-cyclopropanecarboxylate, from Sumitomo.
Sumithrin is a 3-phenoxybenzyl 2-dimethyl-3-(methylpropenyl) cyclopropanecarboxylate, from Sumitomo.
Pynamin Forte ® is a (1R)-cis,trans-chrysanthemic acid, ester with (RS)-allethrolone, from Sumitomo.

The compressed gas propellant may be any suitable conventionally known compressed gas propellant including, but not limited to, air, nitrogen, nitrous oxide, carbon dioxide, argon, methane, ethane, and mixtures thereof. The compressed gas propellant is pressurized in a range from about 100 to 165 psig, preferably from about 120 to 155 psig and more preferably about 135 psig.

The corrosion inhibitor may be any suitable corrosion inhibitor including, but not limited to, phosphates, such as potassium dihydrogen phosphate, potassium hydrogen phosphate, diammonium phosphate, potassium phosphate (monobasic or dibasic), sodium phosphate (monobasic or dibasic); nitrites, such as sodium nitrite, potassium nitrite and ammonium nitrite; and/or aminomethyl propanol.

The antimicrobial may be any antimicrobial including, but not limited to, 2-methyl-2H-isothiazol-3-one, 1,2-benzisothiazol-3(2H)-one, polyhexamethylene biguanide, benzo-iso-thiazolone, 2-methyl-4-isothiazolin-3-one, and/or 3-iodo-2-propynylbutyl carbamate.

The solvent may be any suitable solvent including, but not limited to, alkylene glycols such as propylene glycol and triethylene glycol; glycerin; ethanol; and/or propanol.

The carrier solvent may be any suitable carrier solvent including, but not limited to, water, such as deionized water, distilled water, reverse osmosis water and/or tap water.

Compounds suitable for inclusion as a pH controller include, but are not limited to phosphates, carbonates, borates, and organic acids.

A preferred embodiment of a general composition of the invention is set forth below in Table 2.

TABLE 2

| Component | Wt % (Range) | Function |
|---|---|---|
| Water | 90 to 99 | Carrier Solvent |
| N-Potassium-N-Hydrogen Phosphate | 0.1 to 1 | Corrosion Inhibitor and pH Controller |
| Hydrogenated and Polyethoxylated Castor Oil | 0.06 to 1.9 | Surfactant Solubilizer |
| $C_{6-17}$ Secondary Ethoxylated Alcohol With 3-6 EO | 0.04 to 1.1 | Co-solubilizer |
| Quaternary Ammonium Salt | 0.02 to 0.2 | Co-solubilizer |
| Active Agent | 0.1 to 2 | Active Agent |
| Alkylene Glycol | 0.05 to 2 | Solvent For Surfactant System |
| Antimicrobial | 0.02 to 0.5 | Antimicrobial |
| Compressed Gas | 0.1 to 1 | Propellant |

Preferred embodiments of a composition of the invention wherein the active agent is a fragrance are shown in the Tables below.

TABLE 3

| Component | Wt. % | |
|---|---|---|
| Deionized Water | 96.3 | Carrier Solvent |
| Potassium Dihydrogen Phosphate (5%) and Dipotassium Hydrogen Phosphate (45%) ($KH_xPO_4$, 50% in water) | 1 | Corrosion Inhibitor and pH Controller |
| Hydrogenated and Ethoxylated (60 EO) Castor Oil (40%-100%)) | 0.4 | Surfactant/Solubilizer |
| $C_{6-17}$ Secondary Ethoxylated Alcohol With 3-6 EO | 0.3 | Co-solubilizer |
| Didecyldimethyl ammonium chloride (50%) | 0.1 | Co-solubilizer |
| Fragrance | 0.5 | Active Agent |

TABLE 3-continued

| Component | Wt. % | |
|---|---|---|
| Propylene Glycol | 0.5 | Solvent For Surfactant System |
| Antimicrobial 2-methyl-2H-isothiazol-3-one (2.5%) and 1,2-benzisothiazol-3(2H)one (2.5%) | 0.2 | Antimicrobial |
| Nitrogen Gas (135 psig) | 0.7 | Propellant |

The composition in Table 3 has a total surfactant to fragrance ratio of 1.6:1.

TABLE 4

| Component | Wt. % |
|---|---|
| Deionized Water | 94.1 |
| Potassium Phosphate (50%) | 1 |
| Alkyl Polyglycoside (50%) | 2.5 |
| Fragrance | 0.5 |
| Propylene Glycol | 1 |
| 2-Methyl-4-Isothiazolin-3-one (5%) | 0.2 |
| Nitrogen | 0.7 |

The composition of Table 4 has a total surfactant to fragrance ration of 5:2.

TABLE 5

| Component | Wt. % |
|---|---|
| Deionized Water | 96.3 |
| Potassium Phosphate (50%) | 1 |
| Ethoxylated (60) Hydrogenated Castor Oil (50%) | 0.5 |
| $C_6$-$C_{17}$ Secondary Alcohol (3-6 Mole Ethoxylate) | 0.3 |
| Didecyldimethyl Ammonium Chloride (50%) | 0.1 |
| Fragrance | 0.5 |
| Propylene Glycol | 0.4 |
| Polyhexamethylene Biguanide | 0.2 |
| Nitrogen | 0.7 |

The total surfactant to fragrance ratio for the composition of Table 5 is 1.8:1.

TABLE 6

| Component | Wt. % |
|---|---|
| Deionized Water | 96.3 |
| Potassium Phosphate (50%) | 1 |
| Ethoxylated (60) Hydrogenated Caster Oil (50%) | 0.5 |
| $C_6$-$C_{17}$ Secondary Alcohol (3-6 mole Ethoxylate) | 0.3 |
| Didecyldimethyl Ammonium Chloride (50%) | 0.1 |
| Permethrin | 0.5 |
| Propylene Glycol | 0.4 |
| Polyhexamethylene Biguanide | 0.2 |
| Nitrogen | 0.7 |

The total surfactant to insecticide ratio for the composition of Table 6 is 1.8:1.

By using a compressed gas propellant in the present invention as compared to a standard aerosol propellant, such as a hydrocarbon gas, the composition is able to have a lower amount of a propellant and thereby a reduced amount of surfactant to deliver the same amount of active agent(s), as compared to the amount of surfactant and active agent used with a standard aerosol propellant such as a hydrocarbon. Using lower amounts of surfactant, active agent and propellant are important and beneficial since utilizing less surfactant, active agent, and propellant in the composition decreases the cost of the composition and lower amounts of chemicals are released into the atmosphere as compared to the components from a standard aerosol composition. As set forth above, the reduced amounts of surfactant and active agent, provide for a reduction in stickiness or tackiness of the composition on surfaces upon which particles of the composition fall following use. This is significant since compressed gas aerosols generally have a greater particle size than conventional non-compressed gas aerosols.

The compositions of the invention may be made in any suitable manner and by any suitable means with the understanding that the components are combined so that the active agent(s) are solvated based on combination with the surfactant(s). In a preferred embodiment, the compositions may be made by making an active agent-based solution, e.g., a fragrance-based solution or insecticide-based solution, and combining such solution with a preservative, corrosion inhibitor, water and a compressed gas propellant. With respect to the composition of Table 5, the fragrance-based solution is provided by combining ethoxylated (60 EO) hydrogenated castor oil, the $C_{6-17}$ secondary alcohol with 3-6 EO, the fragrance, the propylene glycol, and the didecyldimethyl ammonium chloride. A combination of the biguanide preservative, the potassium phosphate corrosion inhibitor, and the deionized water is provided. The fragrance-based solution, the solution including the preservative and corrosion inhibitor, and a compressed gas propellant are then combined to make the final product composition, such as shown for example in Table 7.

TABLE 7

| Final Composition | Wt. % |
|---|---|
| Fragrance-Based Solution | 1.8 |
| Preservative Corrosion Inhibitor/Water | 97.5 |
| Compressed Gas Propellant | 0.7 |

Combining the active agent-based solution, e.g., the fragrance-based solution or insecticide-based solution, the solution of a preservative, corrosion inhibitor and water, and the compressed gas propellant may serve to form the final product composition of the invention. However, the components of the present invention may be combined in other suitable manners to make the composition of the invention.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. An aqueous composition pressurized with compressed gas containing at least one active agent comprising:
   about 0.1 wt. % to about 3 wt. % of at least one surfactant;
   about 0.1 wt. % to about 2 wt. % of at least one active agent, wherein said at least one active agent includes at least one of a fragrance or an insecticide;

about 0.1 wt. % to about 1 wt. % of a compressed gas propellant; and 90 wt. % to 99 wt. % of water, wherein said composition, based on the total weight of the composition, has a surfactant to active agent weight ratio of about 1:3 to 5:1, and wherein said at least one active agent is solvated based on combination with said at least one surfactant.

2. The composition of claim 1, wherein said at least one active agent is at least one fragrance.

3. The composition of claim 1, wherein said at least one active agent is at least one insecticide.

4. The composition of claim 1, wherein said at least one surfactant is one or more of an anionic, nonionic, cationic or amphoteric surfactant.

5. The composition of claim 1, wherein said at least one surfactant is a blend of nonionic and cationic surfactants.

6. The composition of claim 1, wherein said at least one surfactant includes at least one of ethoxylated hydrogenated castor oil; ethoxylated hydrogenated castor oil blend; ethoxylated linear alcohol; secondary alcohol ethoxylate; polyglyceryl-10 laurate; polyglyceryl-6 caprylate; ethoxylated $C_6$-$C_{17}$ alcohol; sorbitan monooleate; polyoxyethylene sorbitan monooleate; polyoxyethylene sorbitan monolaurate; alkyl $C_9$-$C_{11}$ polyglycoside; didecyldimethylammonium chloride; didecyldimethylammonium carbonate; polyethyleneoxide/polypropyleneoxide; and mixtures thereof.

7. The composition of claim 1, wherein said compressed gas propellant includes at least one of air, nitrogen, nitrous oxide, argon, carbon dioxide, methane, ethane, and mixtures thereof.

8. The composition of claim 1, further comprising at least one corrosion inhibitor.

9. The composition of claim 8, wherein said at least one corrosion inhibitor is a phosphate, a nitrite, or amino methyl propanol.

10. The composition of claim 1, further comprising at least one solvent.

11. The composition of claim 10, wherein said at least one solvent is one or more alkylene glycol, or mixtures thereof.

12. The composition of claim 1, further comprising at least one antimicrobial.

13. The composition of claim 12, wherein said at least one antimicrobial is a methyl isothiazolone, a benzisothiazolone, a polyhexamethylene biguanide, a carbamate or mixtures thereof.

* * * * *